United States Patent
Viswanadham et al.

(10) Patent No.: US 11,318,452 B2
(45) Date of Patent: May 3, 2022

(54) SINGLE STEP PROCESS FOR THE SIMULTANEOUS PRODUCTION OF AROMATICS, NAPHTHENICS AND ISOPARAFFINS USING TRANSITION METAL FUNCTIONALIZED ZEOLITE BASED CATALYST

(71) Applicant: Council of Scientific & industrial Research, New Delhi (IN)

(72) Inventors: Nagabhatla Viswanadham, Uttarakhand (IN); Anjan Ray, Uttarakhand (IN); Sandeep Kumar Saxena, Uttarakhand (IN); Rajiv Panwar, Uttarakhand (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/937,151

(22) Filed: Jul. 23, 2020

(65) Prior Publication Data

US 2021/0023537 A1 Jan. 28, 2021

(30) Foreign Application Priority Data

Jul. 24, 2019 (IN) .............................. 201911029825

(51) Int. Cl.
*B01J 29/44* (2006.01)
*B01J 37/02* (2006.01)
(Continued)

(52) U.S. Cl.
CPC ............. *B01J 29/44* (2013.01); *B01J 35/002* (2013.01); *B01J 35/0006* (2013.01);
(Continued)

(58) Field of Classification Search
CPC ........ B01J 29/44; B01J 29/46; B01J 37/0207; B01J 37/08; B01J 37/0009; B01J 37/0036;
(Continued)

(56) References Cited

U.S. PATENT DOCUMENTS 4,104,320 A  8/1978  Bernard et al.
4,417,083 A  11/1983  Bernard et al.
(Continued)

FOREIGN PATENT DOCUMENTS

WO   WO-2007/086942 A2   8/2007
WO   WO-2013/165471 A1   11/2013

OTHER PUBLICATIONS

P. W. Tamm, et al., "Octane Enhancement by Selective Reforming of Light Parffins", J. W. Ward, Catalysis 1987, Elsevier Science Publishers B.V., pp. 335-353.

(Continued)

*Primary Examiner* — Elizabeth D Wood
(74) *Attorney, Agent, or Firm* — Blank Rome LLP

(57) ABSTRACT

Hydrocarbon composition plays vital role in fuel quality. For gasoline/motor spirit applications the hydrocarbon should have more octane-possessing molecules from the groups of aromatics, naphthenics and isoparaffins, while n-paraffins are not preferred due to their poor octane. Among the high-octane groups, again aromatics occupy the top but not more than 35 vol % aromatics can be mixed in gasoline for engine applications to avoid harmful emission, But there is no single process that addresses so far the issue of co-producing all the desired hydrocarbon components in a single process. Thus, it is interesting to have a single once-through process working on single catalyst system to produce mixture of all three high-octane molecules namely, aromatics, naphthenics and isoparaffins directly from low- (Continued)

value, low-octane n-paraffin feed. Herein, we report a novel single-step catalytic process for the simultaneous production of aromatics, naphthenics and isoparaffins for gasoline and petrochemical applications.

7 Claims, 3 Drawing Sheets

(51) Int. Cl.
| | |
|---|---|
| B01J 37/08 | (2006.01) |
| B01J 37/00 | (2006.01) |
| B01J 35/00 | (2006.01) |
| B01J 35/02 | (2006.01) |
| C07C 5/27 | (2006.01) |
| C10G 35/085 | (2006.01) |
| C10G 35/09 | (2006.01) |
| C07C 5/373 | (2006.01) |
| C10G 35/06 | (2006.01) |
| C07C 5/333 | (2006.01) |
| C07C 5/22 | (2006.01) |
| C07C 5/32 | (2006.01) |

(52) U.S. Cl.
CPC ......... *B01J 35/023* (2013.01); *B01J 37/0009* (2013.01); *B01J 37/0036* (2013.01); *B01J 37/02* (2013.01); *B01J 37/0207* (2013.01); *B01J 37/08* (2013.01); *C07C 5/222* (2013.01); *C07C 5/2708* (2013.01); *C07C 5/325* (2013.01); *C07C 5/3337* (2013.01); *C07C 5/373* (2013.01); *C10G 35/065* (2013.01); *C10G 35/085* (2013.01); *C10G 35/09* (2013.01); *B01J 2229/20* (2013.01); *B01J 2229/30* (2013.01); *B01J 2229/42* (2013.01); *C10G 2300/305* (2013.01); *C10G 2300/70* (2013.01); *C10G 2400/22* (2013.01); *C10G 2400/30* (2013.01)

(58) Field of Classification Search
CPC .... B01J 37/02; B01J 35/1019; B01J 35/1038; B01J 35/023; B01J 35/0006; B01J 35/002; B01J 2229/20; B01J 2229/30; B01J 2229/42; C10G 2300/70; C10G 2300/305; C10G 2400/30; C10G 2400/22; C10G 35/065; C10G 35/085; C10G 35/09
USPC ...... 502/63, 64, 66, 69, 71, 74, 77; 585/407, 585/734; 208/137, 141
See application file for complete search history.

(56) References Cited

U.S. PATENT DOCUMENTS

| | | | |
|---|---|---|---|
| 4,435,283 A | | 3/1984 | Buss et al. |
| 4,517,306 A | | 5/1985 | Buss |
| 4,784,747 A | * | 11/1988 | Shihabi ................... B01J 29/40 208/111.15 |
| 4,867,864 A | | 9/1989 | Dessau |
| 5,961,818 A | | 10/1999 | Pradhan et al. |
| 7,153,801 B2 | | 12/2006 | Wu |
| 9,051,520 B2 | * | 6/2015 | Batalha ................ B01J 29/7415 |
| 9,598,649 B2 | * | 3/2017 | Nagabhatla .......... C10G 29/205 |
| 2005/0043576 A1 | | 2/2005 | Bournay et al. |
| 2006/0270885 A1 | | 11/2006 | Boyer et al. |
| 2007/0167663 A1 | | 7/2007 | Boyer et al. |
| 2015/0284643 A1 | * | 10/2015 | Nagabhatla ............ C10G 50/00 208/138 |
| 2016/0185687 A1 | | 6/2016 | Parpute et al. |
| 2017/0305862 A1 | * | 10/2017 | Torrens-Jover ...... C07D 231/12 |

OTHER PUBLICATIONS

D. V. Law, et al., "Selective Catalytic Process for Conversion of Light Naphtha to Aromatics", Scopus Preview, Energy Progress, vol. 7, Issue 4, Dec. 1987, pp. 215-222.

* cited by examiner

SINGLE STEP PROCESS FOR THE SIMULTANEOUS PRODUCTION OF AROMATICS, NAPHTHENICS AND ISOPARAFFINS USING TRANSITION METAL FUNCTIONALIZED ZEOLITE BASED CATALYST

RELATED APPLICATION

This application claims the benefit of Indian Patent Application No. 201911029825, filed on Jul. 24, 2019. The entire contents of this application is hereby incorporated by reference.

FIELD OF THE INVENTION

The present invention relates to a single-step catalytic process for the simultaneous production of aromatics, naphthenics and isoparaffins for gasoline and petrochemical applications using transition metal functionalized zeolite based catalyst.

BACKGROUND OF THE INVENTION

The carbon footprint and clean air acts demand the production of neat fuels through environmentally benign processes to serve the society for transportation applications. Increased awareness on the chemical properties of various fuel components and their influence on the quality of the human life helped to set quality specifications for fuels. Especially for gasoline, the demand for high octane on one hand with the simultaneous restrictions on aromatics made paradigm shift to the production of branched paraffins (isoparaffins) as desired gasoline components in this decade.

The paraffin isomerization process has come up to convert not only the non-reformable (through reforming process) n-pentane into high octane isopentane but for the conversion of benzene precursor n-hexane into valuable, high octane gasoline component isohexane. Recently, the n-heptane content in the naphtha is also observed to be processed for isomerization rather than to aromatization so as to control the concentration of total aromatics in the reformate. It is important to note that no single refinery process alone can produce the fuel that can directly be used as gasoline, as every product stream has its own limitations, high aromatics and high benzene limits the direct use of reformate, high sulfur and olefins limits the direct use of FCC gasoline, high RVP limits the direct use of isomerase etc. At present, several refinery streams are combined to make up the final gasoline pool (reformulated gasoline) to meet the fuel specification.

Processing of mixed hydrocarbon feeds such as naphtha or pure feed such as n-heptane is possible either to produce aromatics or isoparaffins at different set of reaction conditions and catalysts due to the fact that the formation of aromatics and isoparaffins are thermodynamically favoured at different set of process conditions; more clearly the formation of aromatics is an endothermic reaction that requires high temperatures while the isoparaffins formation is slightly exothermic and favoured at lower reaction temperatures. In order to meet this, recently combination of three processes is suggested namely, $C_5$-$C_6$ isomerization, $C_7$ isomerization and $C_{8+}$ aromatization to produce $C_5$-$C_7$ isomers and $C_{8+}$ aromatics falling in the gasoline boiling range. The splitting of the feed naphtha ($C_5$-$C_9$) to different carbon cuts, processing them through different catalyst systems and blending them to make final reformulated gasoline is presently followed but is a laborious process.

It is advantageous to have a single process that can produce both aromatics and isoparaffins but there are no reports available with attempts to address the need. Hence, the present invention is aimed to address the issue of simultaneous production of aromatics and isoparaffins by adopting a non-classical approach so as to obtain two important streams of modern gasoline in a single catalyst used single reactor process. A single process producing both aromatics and isoparaffins in a balanced manner from a paraffinic stream is highly desired to meet present and future gasoline specifications. Present study describes a successful attempt to establish a single catalytic process for the simultaneous production of high-octane neat fuel consisting of isomerate along with xylenes and toluene.

Reference may be made to US patent 2016/0185687 A1, where, a sulphated zirconia/alumina based isomerization catalyst was used for effective isomerization of $C_4$-$C_7$ hydrocarbons. This process is aimed to produce isoparaffins but does not produce any aromatics.

Reference may be made to US patent 2006/0270885 A1, WO 2007/086942 A2 and US patent 2007/0167663 A1 where, a process for the isomerization of heptane preferably contained within a naphtha stream is disclosed wherein the naphtha is stripped of the butanes and the pentanes and hexanes are removed for isomerization. The heptanes are fed to a distillation column reactor containing an isomerization catalyst where the normal heptane is isomerized to mono and di branched heptane and removed as overheads. This process does not deal with a single process operating on single catalyst for the simultaneous production of aromatics and isoparaffins.

Reference may be made to US patent 2005/0043576A1, where, a process for the production of an isomerate with a RON that is at least equal to 80 and that contains less than 1% by weight of aromatic compounds, starting with a fraction consisting mostly of hydrocarbons with 7 carbon atoms, and containing paraffins, naphthenes, and aromatic compounds in any proportion is described. But the process uses at least three reactors operating at different conditions one isomerization unit, one unit for opening naphthene rings, and at least one separation unit; these units are combined in such a way as to recycle, to exhaustion, methyl cyclohexane, toluene, and normal paraffins and mono branched paraffins. The process does not describe single process operating on single catalyst without recycle where, aromatics and isoparaffins can be produced simultaneously.

WO 2013/165471 A1 patent application discloses a catalytic process for the production of aromatics through naphtha aromatization using Germanium containing Cs-ZSM-5 catalyst. The examples illustrate the production of aromatics with greater than 80% selectivity to aromatics and there is no disclosure of simultaneous production of isoparaffins along with aromatics in this process.

U.S. Pat. No. 7,153,801 discloses a method of synthesizing a catalyst of a large pore zeolite with platinum incorporation and at least one organic ammonium halide of the formula $N(R)_4X$ where X is a halide and R is a substituted or unsubstituted carbon-chain molecule having 1-20 carbon atoms. The ammonium halide may be an acid halide and an ammonium hydride of the formula $N(R')_4OH$ where R' is hydrogen or a substituted or unsubstituted carbon chain molecule having 12-20 carbon atoms. The catalyst is a bound potassium L-type zeolite (KL zeolite) used to dehydrocyclize aliphatic hydrocarbons ($C_6$-$C_8$ petroleum naphtha) to produce aromatic hydrocarbons (benzene, toluene and xylenes) and there is no disclosure of simultaneous production of isoparaffins along with aromatics in this process.

U.S. Pat. No. 4,867,864 discloses a dehydrogenation/dehydrocyclization process with a non-acidic catalyst of zeolite beta and a dehydrogenation/hydrogenation metal, such as platinum. $C_2$-$C_5$ paraffins are dehydrogenated and C—$C_{12}$ paraffins are dehydrocyclized. The acid content has been reduced by ion-exchange of acid sites with Group IA and/or IIA cations, preferably cesium. Hydrogen must be added during Dehydrocyclizaton and there is no disclosure of simultaneous production of isoparaffins along with aromatics in this process.

U.S. Pat. No. 4,517,306 discloses a catalyst for reforming paraffins containing at least 6 carbon atoms into corresponding aromatic hydrocarbons. The catalyst is a type L zeolite, an alkaline earth metal and a Group VIII metal which has been reduced with hydrogen. One essential element of the catalyst was the presence of the alkaline earth metal which must be barium, strontium or calcium, preferably barium since it lessens the acidity of the catalyst.

U.S. Pat. No. 4,104,320 discloses a method of dehydrocyclizing aliphatic hydrocarbons in the presence of hydrogen to form corresponding aromatic hydrocarbons with a catalyst of a type L zeolite which has at least 90% alkali metal (sodium, lithium, potassium, rubidium, and cesium) exchangeable cations and contains a group VIII dehydrogenating metal and, optionally tin and/or germanium. Again, these metals are added to the catalyst after zeolite synthesis and do not form part of the zeolite framework. No example containing germanium was prepared.

U.S. Pat. No. 4,417,083 discloses a process for production of aromatic hydrocarbons from petroleum fractions containing paraffins in the presence of hydrogen and a catalyst of noble metals and, optionally, sulfur deposited on a crystalline zeolitic aluminosilicate, such as zeolite L, having a pore size of larger than 6.5 Angstroms (Å) and substituted with more than 90% alkali metal cations, such as potassium. It is disclosed that the catalyst can contain rhenium, iridium, tin or germanium in the range of 0-1.5% but no example of a catalyst containing germanium is disclosed. Again, these metals are added to the catalyst after zeolite synthesis and do not form part of the zeolite framework.

U.S. Pat. No. 4,435,283 discloses a method of dehydrocyclizing alkanes, such as n-hexane, with a catalyst of a large-pore zeolite, such as type L zeolite, a Group VIII metal, such as platinum, and an alkaline earth metal (barium, strontium or calcium). Selectivity for n-hexane dehydrocyclization is greater than 60%. The feedstock is substantially free of sulfur and other known poisons for reforming catalysts.

Reference may be made to U.S. Pat. No. 5,961,818, wherein a process for production of LPG and high octane aromatic hydrocarbon from non-economically viable petroleum feedstock through zinc-aluminosilicate molecular sieve (Zn-ZSM-5), in a reactor at a temperature in the range of 300-600° C., pressure 1 to 30 atmosphere liquid hourly space velocity of 1 to 10 hr−1 and nitrogen to hydrocarbon molar ratio 1 to 4, is disclosed. However, this process does not disclose anything related to the isoparaffins production along with aromatics.

The Aromax Process selectively converts $C_6$-$C_7$ paraffins to high octane aromatics utilizing a platinum supported L-type zeolite catalyst of low acidity. A relatively high amount of hydrogen co-feed is required. The Pt/KL zeolite catalyst is used for Octane Enhancement by Selective Reforming of Light Paraffins and there is no disclosure of simultaneous production of isoparaffins along with aromatics in this process [P. W. Tamm. D. H. Mohr, and C. R. Wilson, Catalysis 1987, J. W. Ward (Editor), p. 335-353 (1988). Selective Catalytic Process for Conversion of Light Naphtha to Aromatics, D. V. Law, P. W. Tamm and C. M. Detz, Energy Progress, vol. 7, no. 4, p. 215-222 (December, 1987)].

Based on the prior art details and drawback mentioned above, the object of the present invention is to provide a novel single-step catalytic process for the simultaneous production of aromatics, naphthenics and isoparaffins for gasoline and petrochemical applications.

SUMMARY OF THE INVENTION

Accordingly, the present invention provides a transition metal functionalized zeolite based catalyst possessing both acidity and dehydrogenation functionalities for simultaneous production of aromatics and isoparaffins comprising: a binder and a HZSM-5 zeolite in a weight ratio of zeolite:binder as 3:2;
  wherein the HZSM-5 zeolite has a framework of silicon and aluminum in a ratio of 100-300.

In an embodiment of the present invention, the binder is an inert alumina binder, preferably pseudo boehmite.

In another embodiment of the present invention, the transition metal is selected from platinum (Pt), cobalt (Co), or a combination thereof.

In still another embodiment of the present invention, the surface area of the catalyst is in the range of 350-430 m$^2$/g.

In still another embodiment of the present invention, the total pore volume of the catalyst is in the range of 0.32-0.37 cm$^2$/g.

In still another embodiment of the present invention, the average particle size of the catalyst is in the range of 139-170 Å.

The present invention also provides a process for preparation of a transition metal functionalized zeolite based catalyst possessing both acidity and dehydrogenation functionalities, the process comprising the steps of:
  preparing a support by mixing a H-ZSM-5 zeolite with an inert alumina binder in a weight ratio of 3:2 (zeolite:binder) with continuous grinding to obtain a zeolite-binder support, wherein the H-ZSM-5 zeolite has a framework of silicon and aluminium in a ratio of 100-300, and wherein the alumina binder is pseudo boehmite;
  adding 3 vol % glacial acetic acid to the zeolite-binder support and allowing peptization to obtain a resultant paste;
  wet extruding the resultant paste for formation of wet extrudates, followed by drying and calcination;
  impregnating transition metal on the extrudate by drop-wise addition of a transition metal solution for uniform wet impregnation followed by drying and calcination to obtain the transition metal functionalized zeolite based catalyst, wherein the transition metal is selected from platinum or cobalt or a combination thereof.

In an embodiment of the present invention, a solution of the Co metal is prepared by dissolving cobalt nitrate hexa hydrate salt in distilled water, and a solution of the Pt metal is prepared by dissolving tetra amine platinum (II) nitrate salt in distilled water.

In another embodiment of the present invention, the transition metal functionalized zeolite based catalyst is a bi-metallic catalyst obtained by impregnation of Pt on a cobalt functionalized zeolite extrudate.

The present invention provides a transition metal functionalized zeolite based catalyst produced by the above said process.

The present invention also provides a single-step catalytic process for simultaneous production of aromatics, naphthenics and isoparaffins in presence of a transition metal functionalized zeolite based catalyst, wherein the catalyst has acid sites originated from zeolite material and hydrogenation-dehydrogenation function by presence of a transition metal selected from Pt, Co, or a combination thereof, the process comprising the steps of:
 a. loading the transition metal functionalized zeolite based catalyst as described above into a micro-reactor and reducing the catalyst in presence of continuous hydrogen flow; and
 b. passing a feed over the catalyst obtained in step (a) at a feedstock flow rate ranging from 2-6 WHSV (weight hourly space velocity) and at a reaction temperature ranging from 350-550° C., wherein the feed comprises n-heptane as a source of n-paraffins.

In an embodiment of the present invention, the yields of isoparaffins is in the range of 21 wt % to 72 wt % with aromatics in the range of 7.5 wt % to 63 wt % and naphthenics in the range of 3 to 11 wt. %, and the calculated research octane number (RON) of the product has values ranging from 55 to 94.

BRIEF DESCRIPTION OF THE DRAWING

The present invention is illustrated in figure of the drawing(s) accompanying this specification. In this drawings like reference number/letters indicate corresponding parts in the various figures FIG. 1 describes the isoparaffins and aromatics yield on various catalysts as described in example 11.

DETAILED DESCRIPTION OF THE INVENTION

Figure 1:
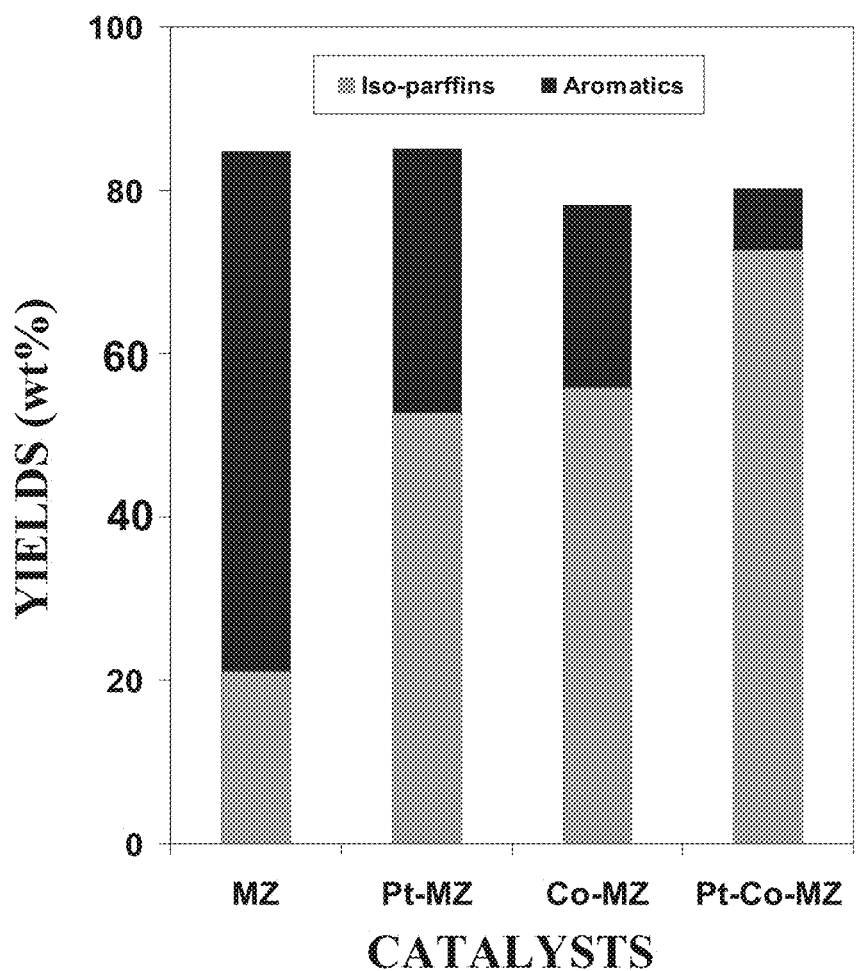

The invention provides a process for the simultaneous production of aromatics, naphthenics and isoparaffins for gasoline and petrochemical applications using a functionalized zeolite based catalyst possessing both acidity and dehydrogenation functionalities so as to facilitate the conversion of n-heptane into low benzene, toluene and xylene rich product also comprising considerable amount of isoparaffins, especially iso-heptane exhibiting higher research octane number at least greater than that of the feedstock where the hike in such octane number may be as high as 80.

The present invention provides a transition metal functionalized zeolite based catalyst comprising: a binder and a HZSM-5 zeolite in a weight ratio of zeolite:binder as 3:2;
 wherein the HZ SM-5 zeolite has a framework of silicon and aluminium in a ratio of 100-300; and
 wherein the catalyst possesses both acidity and dehydrogenation functionalities for simultaneous production of aromatics and isoparaffins In an embodiment, the binder is an inert alumina binder, preferably pseudo boehmite. The transition metal is selected from Pt, Co, or a combination thereof. Further, the surface area of the catalyst is in the range of 350-430 m$^2$/g, total pore volume is in the range of 0.32-0.37 cm$^2$/g, and the average particle size is in the range of 139-170 Å.

The present invention provides a process for preparation of a transition metal functionalized zeolite based catalyst possessing both acidity and dehydrogenation functionalities wherein said catalyst preparation process comprising the steps of:
 a) preparing a support by mixing a H-ZSM-5 with an inert alumina binder in a weight ratio of 3:2 (zeolite:binder) with continuous grinding to obtain a zeolite-binder support, wherein the H-ZSM-5 zeolite has a framework of silicon and aluminium in a ratio of 100-300, and wherein the alumina binder is pseudo boehmite;
 b) adding 3 vol % glacial acetic acid to the zeolite-binder support and allowing it for peptization for 6 h to obtain a resultant paste;
 c) wet extruding the resultant paste through a 2 mm diameter size metallic syringe for formation of wet extrudates, followed by drying at 25° C. to 60° C. temperature for 9 h to 12 h and drying at 100-120° C. for 6 h to 12 h followed by calcination at 500° C. 600° C. for 4 h to 8 h,
 d) impregnating transition metal on the extrudate obtained in step (c) by drop-wise addition of a transition metal solution for uniform wet impregnation followed by drying and calcination to obtain the transition metal functionalized zeolite based catalyst, wherein the transition metal is selected from platinum or cobalt or a combination thereof.

In an embodiment of the present invention, a solution of the Co metal is prepared by dissolving cobalt nitrate hexa hydrate salt in distilled water, and a solution of the Pt metal is prepared by dissolving tetra amine platinum (II) nitrate salt in distilled water.

In an embodiment, the present invention provides cobalt functionalized ZSM-5 zeolites, wherein step (d) of the disclosed process comprises: impregnating 1.2 wt % cobalt on the extrudates by dissolving cobalt nitrate hexa hydrate salt in distilled water (equivalent of water retention volume of HZ-100) to obtain a resultant solution followed by the drop-wise addition of the resultant solution to the zeolite extrudates for uniform wet impregnation of the cobalt salt, followed by drying the extrudates at 25° C. temperature for 12 h and drying at 120° C. for 6 h followed by calcination at 500° C. for 4 h.

In another embodiment, the present invention provides platinum functionalized ZSM-5 zeolites, wherein step (d) of the disclosed process comprises: impregnating 0.6 wt % platinum on the extrudates by dissolving tetra amine platinum (II) nitrate salt in distilled water (equivalent of water retention volume of HZ-100) to obtain a resultant solution followed by the drop-wise addition of the resultant solution to the zeolite extrudates for uniform wet impregnation of the platinum salt, followed by drying the extrudates at 25° C. temperature for 12 h and drying at 120° C. for 6 h followed by calcination at 500° C. for 4 h.

In another embodiment, the present invention provides that the transition metal functionalized zeolite based catalyst is a bi-metallic catalyst obtained by impregnation of Pt on a Co functionalized zeolite extrudate. Further, the present invention provides a process of preparation of cobalt and platinum functionalized ZSM-5 zeolites of silica-to-aluminum ratio 100 so as to prepare efficient bi-metallic catalyst. In a typical procedure the impregnation of 0.6 wt % of the second metal Pt was carried out on 1.2 wt % cobalt ZSM-5 extrudates, wherein tetra amine platinum (II) nitrate salt was dissolved in distilled water (equivalent of water retention volume of HZ-100) followed by the drop-wise addition of the resultant solution to the extrudates for uniform wet impregnation of the platinum salt, followed by drying the extrudates at 25° C. temperature for 12 h and drying at 120° C. for 6 h followed by calcination at 500° C. for 4 h.

The present invention provides a transition metal functionalized zeolite based catalyst produced by the above said process.

The present invention also provides a single-step catalytic process for simultaneous production of aromatics, naphthenics and isoparaffins in presence of a transition metal functionalized zeolite based catalyst, wherein the catalyst has acid sites originated from zeolite material and hydrogenation-dehydrogenation function by presence of a transition metal selected from Pt, Co, or a combination thereof, wherein the process comprises the steps of:
a) loading the transition metal functionalized zeolite based catalyst as described above into a micro-reactor and reducing the catalyst in presence of continuous hydrogen flow at 550° C.; and
b) passing a feed over the catalyst obtained in step (a) at a feedstock flow rate ranging from 2-6 WHSV (weight hourly space velocity) and at a reaction temperature ranging from 350-550° C., and at a pressure of nitrogen ranging from 5-20 bar for the reaction; wherein the feed comprises n-heptane as a source of n-paraffins.

The catalyst exhibits isoparaffins yield in the range of 21-72 wt %, aromatics yield in the range of 7.5-63 wt % and naphthenics yield in the range of 3-11 wt %. The catalyst exhibits stability in activity performance at least up to 42 h.

The Research Octane Number of the product is in the range of 55 to 94.

The single-step catalytic process for the simultaneous production of aromatics, naphthenics and isoparaffins for gasoline and petrochemical applications comprises the sequential steps of:
a) providing the catalyst extrudates with 1-1.5 mm diameter and 2-3 mm length,
b) providing feedstocks such as n-heptane as a source of n-paraffins,
c) providing feedstock flow rate of 2-6 WHSV (weight hourly space velocity),
d) providing reaction temperatures of 350-550° C.,
e) providing nitrogen gas as feed career and as pressurizing gas in the flow rate of 30 lit/h,
f) providing reaction pressure of 5 to 20 bar, and
g) cooling the product gas to obtain liquid and gas products followed by their complete analysis by gas chromatograph.

The work describes the development of zeolite based novel catalytic process which is suitable for the value addition of n-heptane paraffin for the production of isoparaffins along with aromatics which is more suitable for future gasoline production. The gasoline range hydrocarbons include considerable amount of bi-products such as $C_3$ and $C_3^-$. The catalyst exhibits more than 90% conversion of heptane paraffin having Research Octane Number (RON) of about 94 in which the major components are iso-paraffins and aromatics. The low benzene content in the aromatic (gasoline) product makes advantage for its suitability for gasoline applications. The study also envisions the importance of the catalytic properties of modified ZSM-5 zeolite for the production isoparaffins and aromatics in single step conversion of n-heptane. The catalyst is stable in activity up to 42 h without any further regeneration.

The following examples are given by the way of illustration and thereof should not be considered to limit the scope of the invention.

Example 1

This example illustrates the preparation of a series of the catalysts of the invention. The chemical composition of the catalyst is set below in the Table 1. The catalysts were prepared as follows. HZSM-5 zeolites of various silica-to-aluminum ratios were obtained as supports and mixed with pseudo boehmite alumina in the weight ratio of 2:3 (20 g binder for 30 g zeolite) with continuous grinding, followed by drop-wise addition of 25 ml of 3 vol % glacial acetic acid (mixture of 0.75 ml glacial acetic acid and 24.25 ml of distilled water) to the solid mixture and allowing it for peptization for 6 h at room temperature (25° C.). Wet extrusion of the resultant paste was carried out through a 2 mm diameter size metallic syringe for the formation of wet threads, followed by their drying at 25° C. temperature for 12 h and drying at 120° C. for 6 h followed by calcination at 500° C. for 4 h. These catalysts are denoted as HZ-100, HZ-180, HZ-250 and HZ-300 respectively; where the number in parenthesis indicates the silica-to-aluminum ratios of the zeolites HZ-100 which is further denoted as MZ.

Example 2

This example illustrates the preparation of cobalt functionalized ZSM-5 zeolites of silica-to-aluminum ratio HZ-100 (MZ) so as to prepare efficient bi-functional catalyst. In a typical procedure incipient wet impregnation method was used for metal incorporation on HZ-100 support. Impregnation of 1.2 wt % cobalt on the extrudates (10 g) was achieved by dissolving 0.6034 g of cobalt nitrate hexahydrate salt in 5 ml of distilled water (equivalent of water retention volume of HZ-100) followed by the drop-wise addition of the resultant solution to the 10 g zeolite extrudates for uniform wet impregnation of the cobalt salt, followed by drying the extrudates at 25° C. temperature for 12 h and drying at 120° C. for 6 h followed by calcination at 500° C. for 4 h to obtain Co-HZ-100 extrudates denoted as Co-MZ.

Example 3

This example illustrates the preparation of platinum functionalized ZSM-5 zeolites of silica-to-aluminum ratio HZ-100 (MZ) so as to prepare efficient bi-functional catalyst. In a typical procedure we use incipient impregnation method for metal incorporation on HZ-100 support. Impregnation of 0.6 wt % platinum on the extrudates (10 g) was achieved by dissolving 0.1193 g of tetra amine platinum (II) nitrate salt in 5 ml of distilled water (equivalent of water retention volume of HZ-100) followed by the drop-wise addition of the resultant solution to the 10 g zeolite extrudates for uniform wet impregnation of the platinum salt, followed by drying the extrudates at 25° C. temperature for 12 h and drying at 120° C. for 6 h followed by calcination at 500° C. for 4 h to obtain Pt-HZ-100 extrudates denoted as Pt-MZ.

Example 4

This example illustrates the preparation of cobalt and platinum functionalized ZSM-5 zeolites of silica-to-aluminum ratio HZ-100 (MZ) so as to prepare efficient bi-metallic catalyst. In a typical procedure the impregnation of 0.6 wt % the second metal Pt was carried out on Co-MZ extrudates (10 gm), where, 0.1212 g of tetra amine platinum (II) nitrate salt was dissolved in 5 ml of distilled water (equivalent of water retention volume of HZ-100) followed by the dropwise addition of the resultant solution to the 10 g Co-MZ extrudates for uniform wet impregnation of the platinum salt, followed by drying the extrudates at 25° C. temperature for 12 h and drying at 120° C. for 6 h followed by calcination at 500° C. for 4 h to obtain Pt—Co-HZ-100 extrudates denoted as Pt—Co-MZ.

TABLE 1

Chemical composition of the catalysts

| Catalysts | Zeolite (wt %) | Binder (wt %) | Pt metal (wt %) |
|---|---|---|---|
| HZ-100 | 60.0 | 40.0 | 0.0 |
| HZ -180 | 60.0 | 40.0 | 0.0 |
| HZ -250 | 60.0 | 40.0 | 0.0 |
| HZ-300 | 60.0 | 40.0 | 0.0 |
| Co-MZ | 59.4 | 40.0 | 0.0 |
| Pt-MZ | 58.8 | 40.0 | 1.2 |
| Pt—Co-MZ | 58.2 | 40.0 | 1.2 |

Example 5

This example illustrates the physico-chemical properties of the HZ-100 (MZ) and its metal functionalized catalysts i.e. Co-MZ, Pt-MZ and Pt—Co-MZ. As shown in the Table 2, the surface area and pore volume of the metal loaded catalysts are comparable with that of the HZ-100 indicating the absence of pores filling of zeolite channels by bigger metal particles advantageously. The micro pore surface area and micro pore volume were also protected even after metal loading clearly supports the efficient metal functionalization achieved through the impregnation method described in example 2-4. The HRTEM images also support the uniform metal distribution (around 5 nm).

TABLE 2

Physicochemical characterization of various catalysts

| | Characterizations | | | | | | | |
|---|---|---|---|---|---|---|---|---|
| Catalysts | BET Surface Area m²/g | Micropore surface Area m²/g | External Surface Area m²/g | Total pore volume cm³g | Micropore volume cm³/g | Mesopore volume cm³/g | Average particle Size Å | Median pore Å |
| MZ | 391.6983 | 201.2672 | 190.4311 | 0.34030 | 0.08554 | 0.25476 | 153.179 | 24.615 |
| Pt-MZ | 431.5596 | 218.3568 | 213.2028 | 0.37515 | 0.09299 | 0.28216 | 139.031 | 24.523 |
| Co-MZ | 382.8493 | 195.4249 | 187.4244 | 0.33717 | 0.08296 | 0.25421 | 156.720 | 26.114 |
| Pt—Co-MZ | 352.6766 | 189.4536 | 163.2230 | 0.32275 | 0.08006 | 0.24269 | 170.128 | 32.121 |

Example 6

This example illustrates the performance of various H-ZSM-5 catalysts prepared by varying silica-to-alumina ratio of the material, where the number in the sample denotes the silica-to-alumina ratio. The data in table 3 reveals decrease in n-heptane conversion with increased ratios. The yield of aromatics in the product also decreased with conversion but the isoparaffins in the product were formed in higher yields between 100-300 silica-to-alumina ratios. The research octane number (RON) is decreased along with aromatic yields as the aromatics are the main contributors of the RON. The sample HZ-100 (MZ) exhibiting higher conversions, aromatics and RON has been chosen for further catalyst modification so as to facilitate the formation of considerable amount of isoparaffins along with aromatics in the product.

TABLE 3

Catalytic performance of various H-ZSM-5 zeolites in n-heptane conversion

| Catalysts | HZ-100 | HZ-180 | HZ-250 | HZ-300 |
|---|---|---|---|---|
| Conversion (wt %) | 94.3 | 92.7 | 93.3 | 51.1 |
| Liquid yield (wt %) | 50.0 | 69.5 | 68.3 | 46.1 |
| n-Paraffins | 7.7 | 12.0 | 8.5 | 52.0 |
| i-Paraffins | 21.1 | 50.2 | 52.6 | 10.7 |
| Naphthenes | 3.7 | 7.3 | 7.8 | 5.2 |
| Olefins | 1.2 | 4.2 | 2.0 | 3.4 |
| Aromatics | 63.7 | 25.9 | 28.5 | 28.0 |
| Others | 2.6 | 0.4 | 0.6 | 0.7 |
| Total | 100 | 100 | 100 | 100 |
| RON | 94.7 | 75.5 | 75.2 | 52 |

Example 7

This example illustrates the effect of metal functionalization on HZ-100 (MZ) on the catalyst performance in terms of liquid production. The Pt loading on MZ significantly improved the isoparaffin formation where Pt-MZ yields as high as 53 wt % of isoparaffins in the liquid product pool. The aromatic yield at this condition is 32 wt % which is suitable for obtaining high octane liquid pool consisting major amount of isoparaffins along with low aromatics as desired for modern gasoline applications. The RON of this product is 81 stands suitable blending component for gasoline applications. This example also illustrates considerable formation of naphthenics.

TABLE 4

Effect of metal fuctionalization on liquid product yields

| Catalysts | MZ | Pt-MZ | Co-MZ | Pt—Co-MZ |
|---|---|---|---|---|
| Conversion (wt %) | 94.3 | 98.1 | 96.3 | 94.1 |
| Liquid yield (wt %) | 50.0 | 68.0 | 52.0 | 41.0 |
| n-Paraffins | 7.7 | 3.4 | 11.3 | 6.9 |
| i-Paraffins | 21.1 | 52.8 | 55.9 | 72.7 |
| Naphthenes | 3.7 | 8.1 | 5.2 | 11.3 |
| Olefins | 1.2 | 2.9 | 5.0 | 1.5 |

TABLE 4-continued

Effect of metal fuctionalization on liquid product yields

| Catalysts | MZ | Pt-MZ | Co-MZ | Pt—Co-MZ |
|---|---|---|---|---|
| Aromatics | 63.7 | 32.3 | 22.2 | 7.5 |
| Others | 2.6 | 0.5 | 0.4 | 0.1 |
| RON | 94.7 | 81.2 | 78.1 | 55.8 |

Example 8

This example illustrates the effect of metal functionalization on HZ-100 (MZ) on the catalyst performance in terms of gas production. The total gas yield after metal incorporation was not much affected, while C3⁻ olefins (propylene) yield increased from MZ<Pt-MZ<Co-MZ<Pt—Co-MZ (Table 5). This situation is advantageous to produce commercially important propylene as a valuable byproduct.

TABLE 5

Effect of metal fuctionalization on gas product yields

| Catalysts | MZ | Pt-MZ | Co-MZ | Pt—Co-MZ |
|---|---|---|---|---|
| Gas yield (wt %) | 50.0 | 32.0 | 48.0 | 59.0 |
| H$_2$ | 5.9 | 2.5 | 7.9 | 3.8 |
| C1 | 2.1 | 3.9 | 4.2 | 3.3 |
| C2 | 4.3 | 21.6 | 5.8 | 12.7 |
| C2= | 3.4 | 2.9 | 6.9 | 4.9 |
| C3 | 68.9 | 51.7 | 56.7 | 56.8 |
| C3= | 3.5 | 6.0 | 6.4 | 8.1 |
| C4 | 10.5 | 8.5 | 10.0 | 5.0 |
| C4= | 1.4 | 2.9 | 2.1 | 5.4 |
| Total | 100.0 | 100.0 | 100.0 | 100.0 |

Example 9

This example illustrates the effect of cobalt functionalization on HZ-100 on the catalyst performance. As given in Table 4, the Co loading on MZ also significantly improved the isoparaffin formation where Co-MZ yields as high as 56 wt % of isoparaffins in the liquid product pool. The aromatic yield at this condition is 22 wt % which is lower than the aromatics obtained on Pt-MZ. This catalyst is also suitable for obtaining high octane liquid pool consisting major amount of isoparaffins along with low aromatics as desired for modern gasoline applications. The RON of this product is 78 and can be used for gasoline blending applications.

Example 10

This example illustrates the effect of bi-metal functionalization by Pt as well as Co on the catalyst performance. As given in Table 4, the bi-metallic functionalization on HZ-100 resulted in very high increase in isoparaffin formation along with decrease in aromatic formation in the product. Accordingly, the Pt—Co-MZ gives 72 wt % isoparaffins and 7.5 wt % aromatics to contribute 56 RON. Such a high amount of isoparaffins resulted in low RON of 56 in this case. However, this product is suitable as blending component for high-aromatic reformate so as to balance the quality requirement of gasoline for fuel applications.

Example 11

This example demonstrates how the metal functionalization can make possible to cause flexibility in isoparaffins and aromatics yields. As shown in FIG. 1, the relative yields of aromatics and isoparaffins can be obtained on various catalysts. The aromatic yield is highest on MZ whereas, it was lowest on Pt—Co-MZ. The product composition is in between on Pt-MZ and Co-MZ catalysts. Thus, this example illustrates the possible production of varied aromatic and isoparaffins concentrations of the product so as to obtain desired product composition and RON to meet the gasoline blending fuel applications.

Example 12

Figure 2:
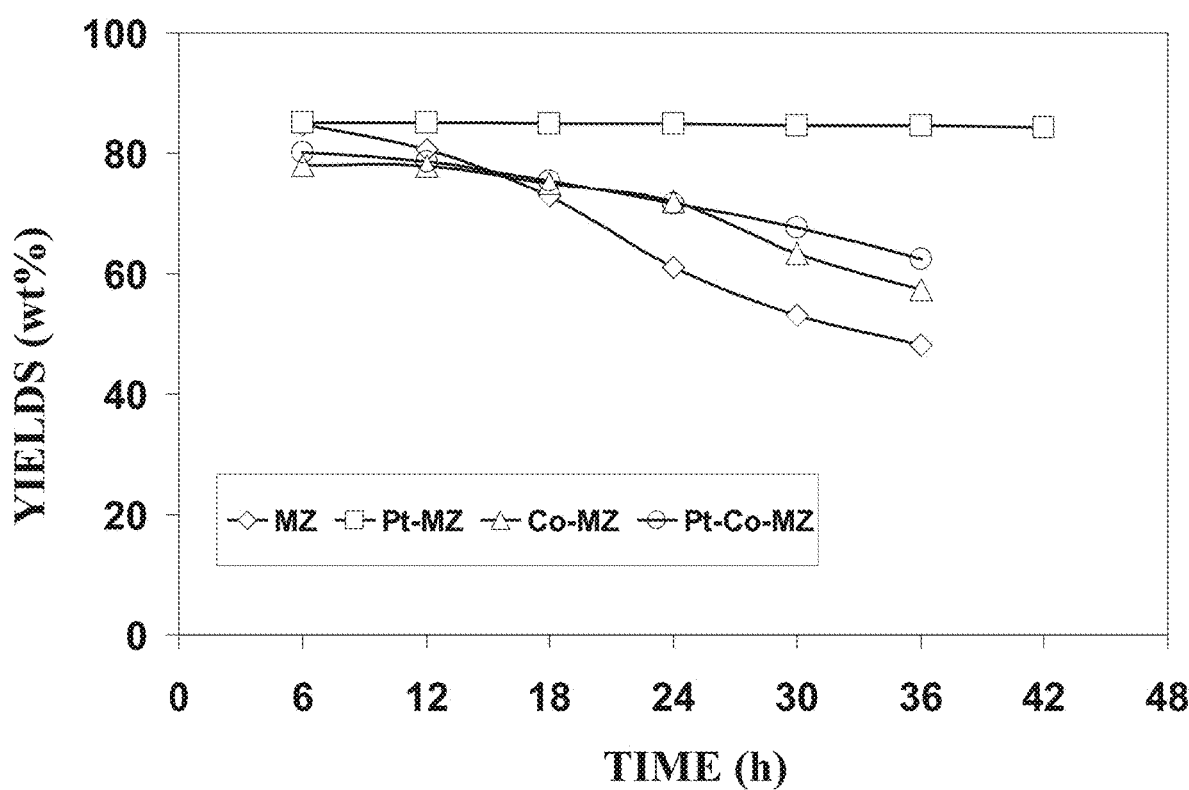
FIG. 2 describes the time on stability performance over various catalysts as described in example 12.

This example illustrates the stability in activity of the various catalysts studied in the reaction of isoparaffins along with aromatics for fuel blending applications. As shown in FIG. 2, the Pt-MZ exhibited stability in activity in terms of product yields (isoparaffins+aromatics) in the studied period of 42 hrs when compared to 18 hrs on Co-MZ and Pt—Co-MZ, while continuous decreased in yields were observed on MZ. Thus Pt-MZ stands as appropriate catalyst for the simultaneous production of aromatics and isoparaffins with stability in activity by virtue of the presence of Pt sites.

Example 13

Figure 3:
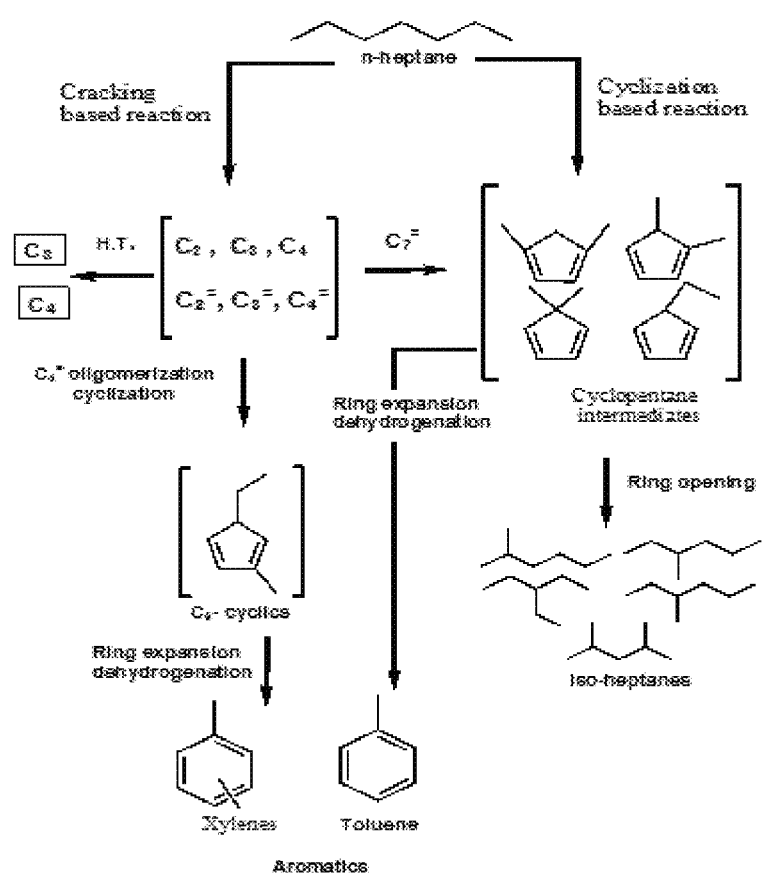
FIG. 3 describes Scheme-1 representing reaction pathways for the simultaneous production of aromatics and isoparaffins from n-heptane feed (reactant).

This example illustrates the reaction pathways for the formation of iso-paraffins at high temperature. As it is well known in the prior art literature that the formation of isoparaffins from the corresponding n-paraffins is possible through hydroisomerizaiton reaction where thermodynamic favors the action equilibrium for isoparaffin production at lower reaction temperatures. Accordingly, the industrial processes for hydroisomerizaiton of n-paraffins work at 130-250° C. and 30 bar pressure to favour the isoparaffin formation. The present process aimed to produce isoparaffins along with aromatics at higher reaction temperatures higher than 400° C. by proving an alternative path for the isomer formation so as to make the product suitable for gasoline fuel applications. As shown in the scheme-1 (FIG. 3) cyclic intermediates are source for the production of aromatics as well as isoparaffins in the present process.

Accordingly, the present invention has fallowing advantages:
1. The present process is capable to convert n-paraffins such as n-heptane into various high-octane molecules such as toluene, xylenes, iso-paraffins and naphthenes suitable for gasoline applications.
2. The present invention provides a single-step process for effective conversion of n-paraffins to various high-octane products.
3. The present invention also works on a single catalyst system that will take care of all the useful reaction steps such as isomerization, cyclization and aromatization involved in the production of valuable high-octane compounds.
4. In the present and future scenario of gasoline specifications, it is advantageous to have the present process which produces balanced hydrocarbon pool having aromatics and isoparaffins so as to meet octane and vapour pressure limitations of the fuels.
5. The present invention also has the advantage of achieving flexible product yields either to increase isoparaffins or aromatics in the product so as to meet the required gasoline blending applications.
6. The product obtained in the present process has the advantage as 80% of the product boils between 40-140°

C. with mid boiling point of at least 90° C. and not more than 120° C. suitable to boil in the gasoline fuel range 7. The process has the advantage with high-octane properties with calculated research octane number (RON) ranging from 55 to 94 suitable for fuel blending applications.

We claim:

1. A catalyst consisting of:
   a binder and a HZSM-5 zeolite in a weight ratio of HZSM-5 zeolite:binder as 3:2;
wherein the HZSM-5 zeolite has a framework of silicon and aluminium in a ratio of 100-300; wherein the HZSM-5 zeolite is a cobalt and platinum functionalized HZSM-5 zeolite, wherein the catalyst is a bi-metallic catalyst, wherein cobalt is from cobalt nitrate hexa hydrate salt, and platinum is from tetra amine platinum (II) nitrate salt, wherein the catalyst has acid sites originating from the presence of the HZSM-5 zeolite and a hydrogenation-dehydrogenation functionality by presence of the cobalt and platinum, wherein the catalyst is effective to promote a simultaneous production of aromatics, naphthenics and isoparaffins from n-heptane, and wherein a conversion of the n-heptane is 94.1 wt %.

2. The catalyst as claimed in claim 1, wherein the binder is an inert alumina binder, and wherein the binder is pseudo boehmite.

3. The catalyst as claimed in claim 1, wherein the catalyst has a surface area in a range of 350-430 m$^2$/g, a total pore volume in a range of 0.32-0.37 cm$^2$/g, and an average particle size in a range of 139-170 Å.

4. A process for preparing a catalyst, the process consisting of:
   a. preparing a support by mixing a H-ZSM-5 zeolite with an inert alumina binder in a weight ratio of 3:2 (zeolite:binder) with continuous grinding to obtain a zeolite-binder support, wherein the H-ZSM-5 zeolite has a framework of silicon and aluminium in a ratio of 100-300, and wherein the alumina binder is pseudo boehmite;
   b. adding 3 vol % glacial acetic acid to the zeolite-binder support and allowing peptization to obtain a resultant paste;
   c. wet extruding the resultant paste for formation of wet extrudates, followed by drying and calcination;
   d. impregnating cobalt on the extrudate obtained in step (c) by drop-wise addition of a solution of cobalt nitrate hexa hydrate salt for a uniform wet impregnation to obtain a cobalt functionalized zeolite extrudate followed by impregnating platinum on the cobalt functionalized zeolite extrudate by drop-wise addition of a solution of tetra amine platinum (II) nitrate salt for a uniform wet impregnation followed by drying and calcination to obtain the catalyst, wherein the catalyst is a bi-metallic catalyst, wherein the catalyst has acid sites originating from the presence of the HZSM-5 zeolite and a hydrogenation-dehydrogenation functionality by presence of the cobalt and platinum, wherein the catalyst is effective to promote a simultaneous production of aromatics, naphthenics and isoparaffins from n-heptane, and wherein a conversion of the n-heptane is 94.1 wt %.

5. The process as claimed in claim 4, wherein the solution of cobalt nitrate hexa hydrate salt is prepared by dissolving the cobalt nitrate hexa hydrate salt in distilled water, and the solution of tetra amine platinum (II) nitrate salt is prepared by dissolving the tetra amine platinum (II) nitrate salt in distilled water.

6. A single-step catalytic process for simultaneous production of aromatics, naphthenics and isoparaffins the process consisting of:
   a. preparing a support by mixing a HZSM-5 zeolite with an inert alumina binder in a weight ratio of 3:2 (zeolite:binder) with continuous grinding to obtain a zeolite-binder support, wherein the HZSM-5 zeolite has a framework of silicon and aluminium in a ratio of 100-300, and wherein the alumina binder is pseudo boehmite;
   b. adding 3 vol % glacial acetic acid to the zeolite-binder support and allowing peptization to obtain a resultant paste;
   c. wet extruding the resultant paste for formation of wet extrudates, followed by drying and calcination;
   d. impregnating cobalt on the extrudate obtained in step (c) by drop-wise addition of a solution of cobalt nitrate hexa hydrate salt for a uniform wet impregnation to obtain a cobalt functionalized zeolite extrudate followed by impregnating platinum on the cobalt functionalized zeolite extrudate by drop-wise addition of a solution of tetra amine platinum (II) nitrate salt for a uniform wet impregnation followed by drying and calcination to obtain a catalyst, wherein the catalyst is a bi-metallic catalyst, wherein the catalyst has acid sites originating from the presence of the HZSM-5 zeolite and a hydrogenation-dehydrogenation functionality by presence of the cobalt and platinum, wherein the catalyst is effective to promote a simultaneous production of aromatics, naphthenics and isoparaffins from n-heptane, and wherein a conversion of the n-heptane is 94.1 wt %;
   e. loading the catalyst into a micro-reactor and reducing the catalyst in presence of a continuous hydrogen flow; and
   f. passing a feed over the catalyst obtained in step (a) at a feedstock flow rate ranging from 2-6 WHSV (weight hourly space velocity) and at a reaction temperature ranging from 350-550° C.; wherein the feed consists of n-heptane.

7. The process as claimed in claim 6, wherein yields of isoparaffins are 72.7 wt % with aromatics and naphthenics in an amount of 7.5 wt % and 11 wt. %, respectively, and with a calculated research octane number (RON) of 56.

* * * * *